(12) United States Patent
Nashed (10) Patent No.: US 8,550,076 B2
(45) Date of Patent: Oct. 8, 2013

(54) VACUUM ATTACHMENT AND BREATHING CIRCUIT APPARATUS

(76) Inventor: Ramses Nashed, Tierra Verde, FL (US)

( * ) Notice: Subject to any disclaimer, the term of this patent is extended or adjusted under 35 U.S.C. 154(b) by 554 days.

(21) Appl. No.: 12/800,626

(22) Filed: May 19, 2010

(65) Prior Publication Data

US 2010/0229861 A1    Sep. 16, 2010

Related U.S. Application Data (63) Continuation-in-part of application No. 12/658,019, filed on Feb. 1, 2010, which is a continuation-in-part of application No. 12/455,048, filed on May 28, 2009, now abandoned, which is a continuation-in-part of application No. 12/221,379, filed on Aug. 1, 2008, which is a continuation-in-part of application No. 11/809,435, filed on Jun. 1, 2007, now Pat. No. 8,336,549.

(51) Int. Cl.
*A61M 16/00* (2006.01)

(52) U.S. Cl.
CPC .................................... *A61M 16/00* (2013.01)
USPC ............ 128/203.28; 128/200.24; 128/203.12; 128/203.15; 128/203.25; 128/205.13

(58) Field of Classification Search
USPC ............. 128/200.24, 200.11–200.23, 203.12, 128/203.15, 203.29, 205.25, 206.21, 206.23, 128/206.24, 206.27, 206.28, 207.11
See application file for complete search history.

(56) References Cited

U.S. PATENT DOCUMENTS

| | | | | |
|---|---|---|---|---|
| 3,467,092 | A | * | 9/1969 | Bird et al. ................ 128/204.25 |
| 4,219,020 | A | * | 8/1980 | Czajka ..................... 128/207.13 |
| 4,265,239 | A | * | 5/1981 | Fischer et al. ........... 128/205.17 |
| 4,520,808 | A | * | 6/1985 | LaBauve .................. 128/200.14 |
| 4,770,169 | A | * | 9/1988 | Schmoegner et al. ... 128/207.13 |
| 4,794,921 | A | * | 1/1989 | Lindkvist ................ 128/203.29 |
| 4,807,617 | A | * | 2/1989 | Nesti ....................... 128/205.12 |
| 5,404,873 | A | * | 4/1995 | Leagre et al. ............ 128/204.18 |
| 5,485,835 | A | * | 1/1996 | Vande Streek et al. .. 128/205.13 |
| 7,900,633 | B2 | * | 3/2011 | Sinha ....................... 128/207.14 |
| 8,333,198 | B2 | * | 12/2012 | Sinha ....................... 128/207.14 |
| 2001/0025641 | A1 | | 10/2001 | Doane et al. |
| 2008/0295845 | A1 | | 12/2008 | Nashed |

* cited by examiner

*Primary Examiner* — Annette Dixon
(74) *Attorney, Agent, or Firm* — Ronald E. Smith; Smith & Hopen, P.A.

(57) ABSTRACT

An ambient or room air vacuum attachment or nozzle is provided proximal to the connection between a breathing circuit and the protruding inlet port of a respiratory face mask, and a tubular passageway is sealingly connected between the vacuum attachment or nozzle and a source of vacuum. By virtue of such structure, any gas escaping from the periphery of the respiratory face mask through accident or otherwise is immediately and automatically "vacuumed-up" by the proximally located vacuum attachment or nozzle and evacuated from the surrounding room environment through the vacuum source to which the ambient air vacuum nozzle and tubular passageway are connected.

1 Claim, 5 Drawing Sheets

VACUUM ATTACHMENT AND BREATHING CIRCUIT APPARATUS

RELATED APPLICATIONS

The present application claims priority and is a continuation-in-part of U.S. patent application Ser. No. 12/658,019, filed Feb. 25, 2010, which is a continuation-in-part of U.S. patent application Ser. No. 12/455,048, filed May 28, 2009 now abandoned which is a continuation-in-part of U.S. patent application Ser. No. 12/221,379, filed Aug. 8, 2008, which is a continuation-in-part of U.S. application Ser. No. 11/809,435, filed Jun. 1, 2007, now U.S. patent No. 8,336,549. Each of said related applications is hereby incorporated by reference into this application.

BACKGROUND OF THE INVENTION

1. Field of the Invention

The present application relates generally to devices for delivering respiratory gas or gases in medical applications, and more particularly, to a new and improved vacuum attachment and breathing circuit apparatus especially useful in administering gases, such as anesthesia inhalation agents; or oxygen, or air, or mixtures of same, for medical purposes, and constitutes an improvement over the similar device or other devices disclosed in my prior applications.

2. Description of the Prior Art

As disclosed in my prior applications, it is quite well known to use nitrous oxide ($N_2O$)n gas inhalation form as a safe and effective sedation anesthetic. This compound, frequently called "laughing gas" or "happy gas," has been used medically for many years usually as an analgesic or "light sedative" to ease pain associated with trauma, childbirth or heart attacks, for example, or as a carrier for more potent anesthesia gases (e.g. Desflurane, Sevoflurane). Indeed, nitrous oxide is so safe, easy to handle, and readily available relatively inexpensively, it has been used as an anesthetic in dentistry since the 1800s. When used by a dentist, nitrous oxide is typically administered through a demand-valve or continuous inhaler placed over the patient's nose so that the patient's mouth can be worked on while the patient continues to inhale the gas. A full face-mask therefore cannot be used in dentistry, and to avoid build-up of exhaled or waste nitrous oxide, which can pose an intoxicating and prolonged-exposure hazard to the clinic staff in the room where the procedure is being conducted, a continuous-flow-fresh-air ventilation system or nitrous-scavenging system must be used.

In "*Case Series of Nurse-Administered Nitrous Oxide for Urinary Catheterization in Children,*" *Anesthesia & Analgesia* 2007; 104:876-879, Judith L. Zier, M. D. et al, the authors reported the use of $N_2O$ to "sedate" children undergoing a painful procedure in a hospital setting. Administration of the nitrous was carried out using commercially available "dental" equipment to supply the $N_2O$ gas and to scavenge exhaled waste (through a nose mask). Thus, the authors reported that a "comfortable seal could be maintained . . . over the nose of the older child" (emphasis added). Nitrous oxide is only minimally metabolized in the human body. Accordingly, unless provision is made to collect or otherwise scavenge the breath of a patient exhaled through the mouth, build up of exhaled $N_2O$ waste gas in the hospital environment using such "dental equipment" cannot reasonably be avoided.

In order to overcome the foregoing disadvantages, in my prior application Ser. Nos. 12/658,019 and 12/455,048, I disclose new and improved respiratory face mask and breathing circuit assemblies adapted to be used with commercially available nitrous oxide gas handling equipment commonly and heretofore used in "dentistry." When so employed, these disclosed respiratory face mask and breathing circuit assemblies have been found to minimize build-up of waste $N_2O$ gas in the surrounding environment sufficiently to facilitate safe and effective use of such devices or equipment for "sedation" purposes in a hospital or other clinical environment.

Nonetheless in those instances when and where the respiratory face mask is inadvertently momentarily lifted off the face of a patient undergoing nitrous sedation by jostling of the patient or otherwise, it is still possible for a minor amount of nitrous oxide gas to escape around the periphery of the face mask into the surrounding environment. It would be a desirable advantage to be able to automatically and rapidly capture and remove such escaping nitrous gas (scavenge) even in minute quantities, during normal operation of the respiratory face mask and breathing circuit assemblies heretofore disclosed in my prior applications. Such need is met by the new and improved "vacuum attachments" of the present invention.

BRIEF SUMMARY OF THE INVENTION

The present invention, briefly described, provides novel vacuum attachments to be employed with a breathing circuit adapted to be operatively coupled at one end thereof to the protruding inlet port of a respiratory face mask wherein the breathing circuit is adapted to supply inspired fresh gas to a patient and to evacuate exhaled waste gas in a hospital setting. An ambient or room air vacuum attachment or nozzle is provided proximal to the connection between the breathing circuit and the protruding inlet port of the face mask, and a tubular passageway is sealingly connected between the vacuum attachment or nozzle and a source of vacuum. By virtue of such structure, any gas escaping from the periphery of the respiratory face mask through accident or otherwise is immediately and automatically "vacuumed-up" by the proximally located vacuum attachment or nozzle and evacuated from the surrounding room environment through the vacuum source to which the ambient air vacuum nozzle and tubular passageway are connected.

There has thus been described, rather broadly, several important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining the further alternatively preferred embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved breathing circuit apparatus which has all of the advantages of the prior art and none of the disadvantages.

It is another object of the present invention to provide a new and improved breathing circuit apparatus that is especially suitable for use in administering anesthesia inhalation gas or gases to a patient continuously without causing any exhaled waste gas to build-up in the surrounding area.

It is yet a another object of the present invention to provide a new and improved breathing circuit apparatus which is of durable and reliable construction.

An even further object of the present invention is to provide a new and improved breathing circuit apparatus which is susceptible of a low cost of manufacture with regard to both materials and labor, and which accordingly is then susceptible of low prices of sale, thereby making such a face mask and breathing circuit assembly economically available to the medical community.

Even still another object of the present invention is to provide a new and improved breathing circuit apparatus that may be used on a patient in a hospital or clinical setting in a safe and effective manner.

It is yet another object of the present invention to provide a new and improved breathing circuit apparatus adapted to be coupled to the fresh gas supply module of a nitrous oxide "dental set" and further includes means for scavenging outside room air proximal to the connection between the breathing circuit and a respiratory face mask.

Still yet another object of the present invention is to provide a new and improved breathing circuit apparatus where the breathing circuit is adapted to be connected to a respiratory face mask and means are provided for effecting continuous scavenging of outside room air proximal to the connection between the breathing circuit and the respiratory face mask.

Yet still another object of the present invention is to provide new and improved vacuum attachments for a breathing circuit where the breathing circuit is adapted to be connected to a respiratory face mask inlet and the vacuum attachments are provided for effecting continuous scavenging of ambient or outside room air proximal to the connection between the breathing circuit and the respiratory face mask inlet by a convenient vacuum source connected to the breathing circuit.

Still yet another object of the present invention is to provide new and improved vacuum attachments for a breathing circuit apparatus where the breathing circuit is connected to a face mask via an inlet port on the face mask and wherein the vacuum attachments comprise a suction nozzle for effecting continuous vacuum suctioning of ambient air proximal to the respiratory face mask inlet, and wherein the suction nozzle comprises an annular-shaped chamber encircling the face mask inlet when the breathing circuit is connected to the inlet, and wherein a tubular passageway is provided having opposed first and second ends with the tubular passageway first end being connected to the annular-shaped chamber and the tubular passageway second end adapted to be connected to a vacuum source.

Yet still another object of the present invention is to provide a new and improved breathing circuit apparatus where the breathing circuit is connected to the face mask inlet by an elbow connector and vacuum attachments are provided for effecting continuous vacuum suctioning of ambient air proximal to the elbow connector and face mask inlet, the vacuum attachments in one preferred form comprising an annular wall on said elbow, a closed passageway having opposed first and second ends, wherein the first end of said passageway is connected to said annular wall and the second end of said passageway is connected to the vacuum switch or module of a nitrous gas "dental" set-up or Flowmeter through a branched vacuum connector, wherein said breathing circuit has an exhalation reservoir bag connected distally with respect to said elbow, said reservoir bag has an opening at one end thereof, and wherein said branched vacuum connector also is connected to said exhalation bag through said opening at one end thereof.

These together with additional objects of the invention, along with, the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the present invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference initially to FIGS. 1-6 of the Drawings, wherein like reference numerals refer to like parts already described in connection with applicant's prior embodiments as disclosed in his prior applications, a further alternatively preferred embodiment of the present continuation-in-part application is shown generally comprising a face mask 10, a uniquely modified breathing circuit 90', and a gas supply and scavenging device 100.

Figure 1:
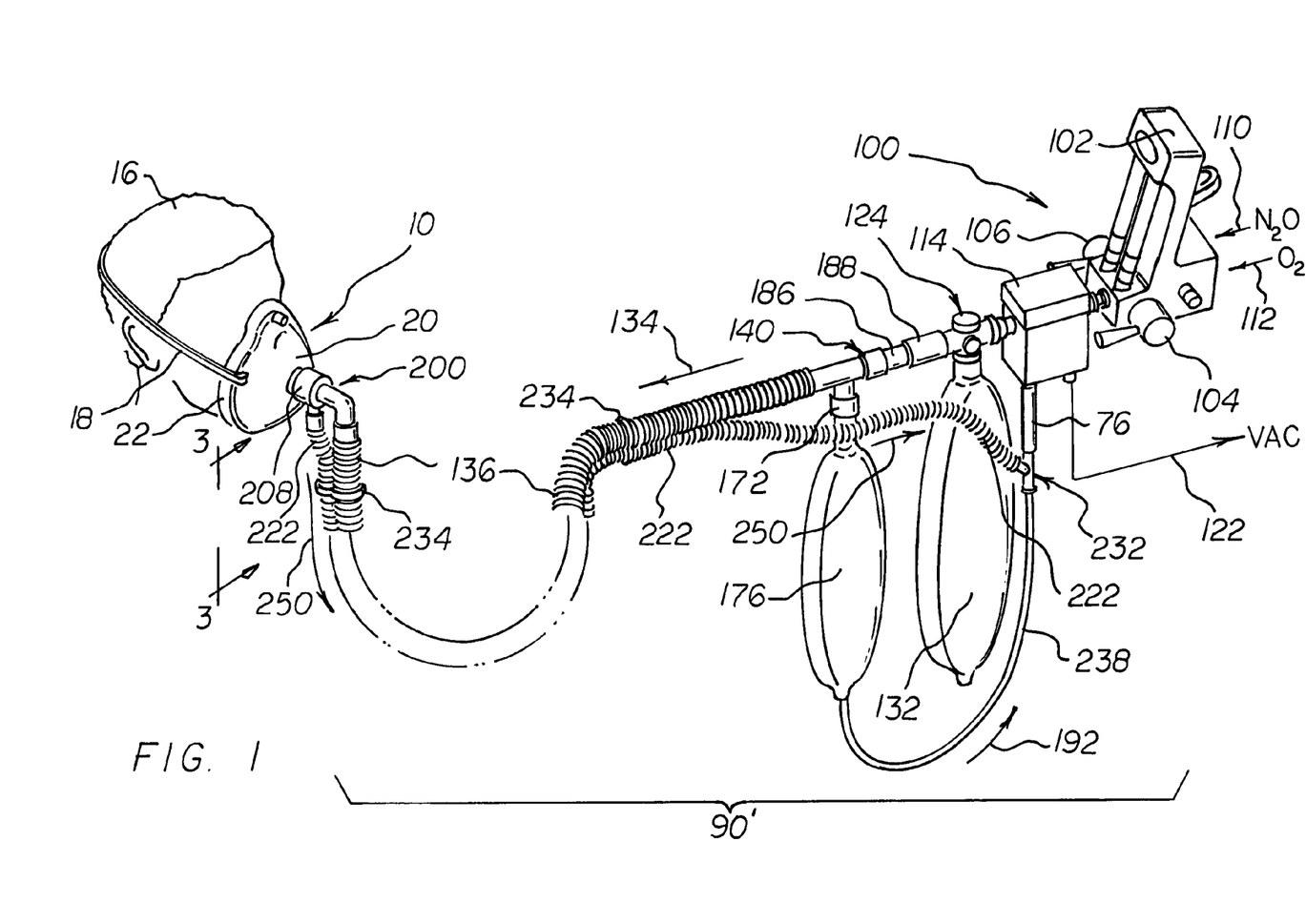
FIG. 1 is a schematic depiction in perspective of the first preferred embodiment of the vacuum attachment and breathing circuit apparatus according to the present invention connected between a respiratory face mask and a "dental" set-up Flowmeter.

As schematically depicted in FIG. 1, face mask 10 is adapted to be fitted on the face of a patient 16 via optional headstrap 18 (preferably elastic) removably attachable to the face mask via anchors or the like on the opposed edges thereof. The headstrap helps to stabilize the mask on the face and head of a person, preferably before, during and/or after surgery. Face mask 10 can be the disposable anesthesia face mask of my prior applications and in particular, the disposable anesthesia face mask fully disclosed in U.S. patent document 2008/0295845 (Nashed), published Dec. 4, 2008 (incorporated herein by reference), which is mostly preferred. While the details of the face mask disclosed in the latter patent document are outside the scope of the present invention, suffice it to say for purposes of fully understanding the present invention, the mostly preferred face mask 10 comprises a cup-like shell or receptacle member 20, typically of molded transparent plastic (e.g. PVC), and a flexible pneumatic (inflatable) cushion member 22. The flexible pneumatic inflatable cushion member 22 defines a generally donut-shaped sealing member extending annually along the entire extent of a peripheral rim or flange defined by the shell member 20. The crown portion of shell member 20 has a substantially cylindrically-shaped extension defining a hollow inlet member or port 26 protruding therefrom. Face mask inlet port 26 is suitably sized with an inside diameter "d" (FIG. 4) to removably receive therein in a snug sliding (and sealing) relationship the connection nipple on a breathing circuit, and to thereby define a passageway such that anesthesia gas or other gases (e.g. nitrous oxide, oxygen, or mixtures of same) are adapted to pass from a source through the breathing circuit, the connection nipple and the passageway into the interior of shell member 20.

The breathing circuit also is adapted to receive returned or exhaust gas or gases exhaled by the patient through the same passageway and connection nipple and convey such exhausted gas or gases to a gas evacuation or scavenging apparatus which in the context of the present invention preferably comprises a gas device (or Flowmeter) 100 of the type commonly used in dentistry for "sedation" purposes, that is to apply inspired nitrous oxide (or a mixture of nitrous and oxygen) to a patient through a dental nasal mask.

In contrast to the nasal mask conventionally used in dentistry, when the mostly preferred face mask 10 is applied to a patient, the top portion of the mask shell 20 receives and covers the nose portion of the patient, the intermediate portion of mask shell covers the mouth portion of the patient, and the bottom or widest portion of the mask shell receives and engages the underside of the chin and jaw portion of the patient's face with the pneumatic cushion member 22 effectively serving to seal the periphery of the mask shell 20 relative to the patient's irregular facial contour and prevent escape of anesthesia gas or other gas into the surrounding environment. As further disclosed in US patent document 2008/0295845, the foregoing engagement between the underside of the chin or jaw portion of the patient with the bottom or widest transverse edge portion of the mask shell and cushion prevents displacement of the mask toward the ocular area, helps to keep the patient's mouth closed, and helps to securely stabilize the mask assembly on the patient's face.

Notwithstanding the foregoing, it will understood that in carrying out the present invention a conventional disposable anesthesia face mask such as that depicted in FIG. 4 of U.S. patent document 2001/0025641 (Doane et al.), published Oct. 4, 2001, incorporated herein by reference, alternatively may be used in lieu of the face mask disclosed in U.S. patent document 2008/0295845. Such conventional disposable anesthesia face masks generally are oval-shaped and merely cover the nose and mouth portion of a patient's face and therefore must be held in place by anesthesia personnel or another care provider, or held on the patient's face by a relatively tightly-wound strap.

Figure 2:
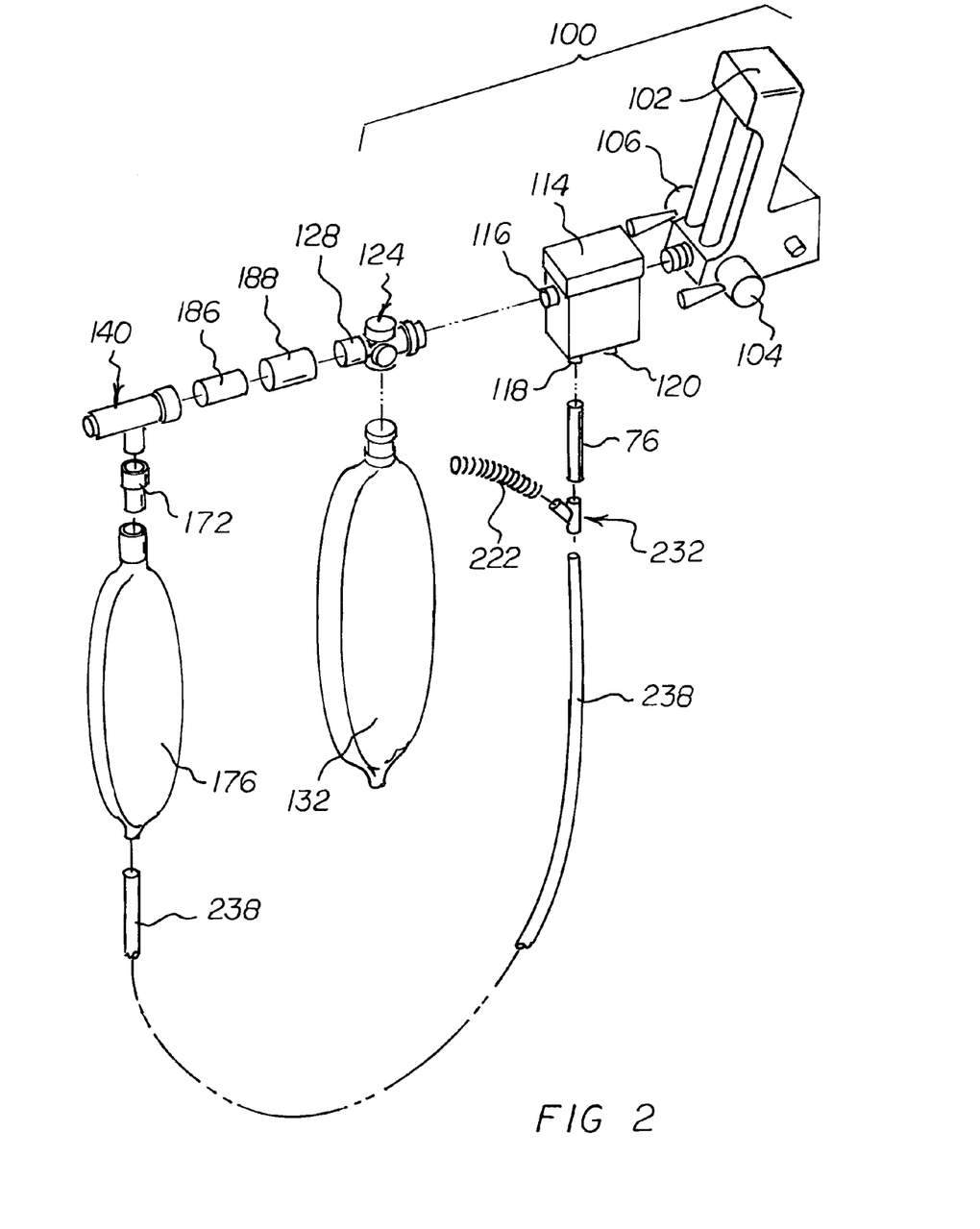
FIG. 2 is an exploded view in perspective of a portion of the embodiment and of the components of the breathing circuit apparatus and "dental" set-up depicted in FIG. 1.

The breathing circuit 90' generally speaking can be employed to deliver nitrous oxide, oxygen, or mixtures of same, originating from a gas supply and scavenging device 100 to the mostly preferred face mask 10. As schematically depicted in FIGS. 1 and 2, gas supply and scavenging device 100 preferably comprises a "dental" set-up commercially made available by Porter Instrument, Hatfield, Pa. 19440 under the designation "MXR Flowmeter." Typically, this apparatus is mounted on a post supported by a wheeled dolly to render the entire unit portable, or the device may be more permanently mounted on a wall surface via a pivotal bracket or the like. Additionally, it will be appreciated that the MXR Flowmeter device 100 (hereinafter sometimes "Flowmeter") is located proximal to a supply of fresh inhalation gas or gases such as nitrous oxide and oxygen, for example, and to a source of vacuum, which sources may be made available through a conveniently located wall outlet, and coupled to the Flowmeter device 100 via suitable flexible hoses or tubing, all as is well known in the anesthesia art and the art of such "dental" devices.

As even further schematically depicted in FIGS. 1 and 2, Flowmeter 100 includes a fresh gas mixing console 102 having valve controls 104, 106 for oxygen ($O_2$) and nitrous oxide ($N_2O$), respectively, which when suitably manipulated can produce an output flow of a desired selected mixture of these two gases through an output nozzle 108. As mentioned, Flowmeter 100 suitably is adapted to be connected to a source of nitrous oxide and a source of oxygen as schematically indicated by arrows 110 and 112, respectively. Nozzle 108, in turn, suitably is connected to an automatic vacuum switch (AVS) module 114 having a fresh (mixed) gas output nozzle 116, a mask-to-vacuum input nipple or nozzle 118 and vacuum-to-source output nipple or nozzle 120. Nipple 118 is adapted to be connected to the distal end of the exhalation limb of breathing circuit 90' (as will be explained in more detail below) whereas nozzle 120 is adapted to be connected to a conventional source of "always on" vacuum as schematically indicated by arrow 122 preferably via a suitable flexible hose or tube and vacuum wall outlet (not shown). It will be noted that the AVS module 114 includes a safety switch that operates to automatically cut-off the vacuum into the module if the flow of mixed gas (e.g. nitrous/oxygen) through the module is interrupted for any reason during operation of the Flowmeter 100.

Output nozzle 116 of AVS module 114 suitably is connected to "Bag Tee" coupling 124 which includes an internal passage (not shown) extending between output nozzle 116 and a first output nozzle 126 on the "Bag Tee" coupling. First output nozzle 126, in turn, is connected to the cylindrical input collar 130 of closed-end flexible reservoir bag 132. The "Bag Tee" coupling 124 further includes a second internal passage (not shown) connected between input collar 130 and a second output nozzle 128 (FIG. 2). By this arrangement, any flow of gas (or gas mixture) from nozzle 116 will enter flexible reservoir bag 132 before exiting the "Bag Tee" through second output nozzle 128. Additionally, a uni-directional demand valve (not shown) suitably is included inside of second output nozzle 128 such that any fresh gas (or gas mixture) stored inside flexible reservoir bag 132 is adapted to flow in the direction of arrow 134 when a patient 16 inhales through face mask 10 and breathing circuit 90' of the present invention as will be discussed in greater detail below.

Flowmeter console 102, switch module 114, Bag Tee coupling 124 and flexible reservoir bag 132 are part and parcel of a conventional "dental" set-up (e.g. MXR Flowmeter) in widespread use for delivering nitrous oxide to a patient in a dentist's chair through a nasal mask and therefore the specific details of construction of these components are well known and understood, forming no part of the present invention. When so employed, dental patients invariably exhale unmetabolized nitrous oxide into the room environment by exhaling through their mouth making the use of such equipment unsuitable in a hospital or other clinical environment for "sedation" or other purposes.

In accordance with the present invention, breathing circuit 90' can be used with face mask 10 and Flowmeter 100 to dramatically minimize the escape of nitrous oxide into the surrounding room environment and therefore to facilitate the safe and effective use of nitrous oxide or other inhalation gases in a hospital or clinical setting where build-up of exhaled waste gas or gases may not be tolerated.

Figure 3:
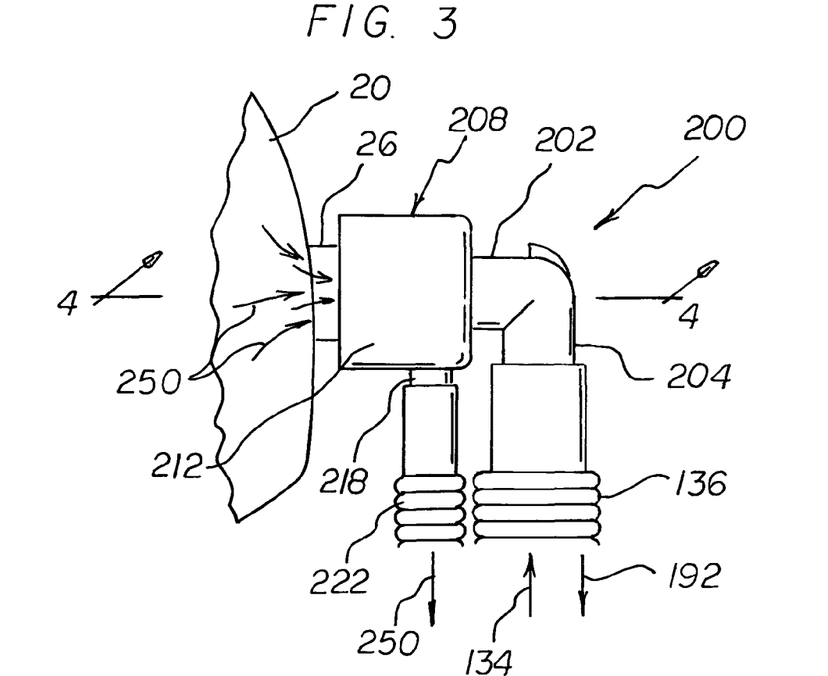
FIG. 3 is an enlarged fragmentary view in elevation of a portion of FIG. 1 showing the connection between breathing circuit 90' and the inlet port of respiratory face mask 10 taken along line 3-3 in FIG. 1.
Figure 4:
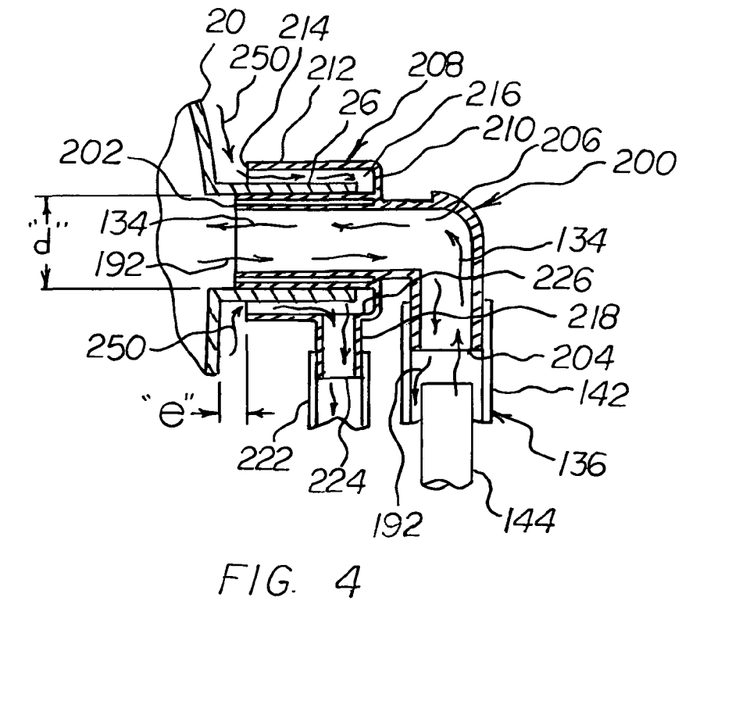
FIG. 4 is a cross-sectional view of the breathing circuit and face mask inlet port connection of FIG. 3 taken along line 4-4 of FIG. 3.

To this end, breathing circuit 90' includes a first length of flexible tubing 136 adapted to be removably sealingly coupled at a first end thereof to face mask 10. Preferably, and for this purpose, the aforementioned first end of tubing 136 has sealingly connected to it a suitable right-angle tube coupling or "elbow" connector generally indicated by reference sign 200. Substantially as depicted in FIGS. 3 and 4, elbow 200 has a first input end 202 suitably sized and configured to be removably sealingly and slidingly fitted into the opening defined by the protruding cylindrical port 26 of the face mask 10. Elbow 200 also has an opposed, substantially right-angle disposed other or second end 204 suitably sized and configured to be sealingly secured to the aforementioned first end of breathing circuit flexible tubing 136, as is well known in this art. The tube coupling elbow 200 has a hollow preferably substantially cylindrically-shaped interior extending axially between its first input end 202 and its opposed second other end 204 defining an L-shaped flow passageway 206 between the first end of flexible tubing 136 and the interior of mask shell 20 when the first input end 202 is sealingly and slidingly axially inserted into opening "d" defined by mask inlet port 26.

The first length of flexible tubing 136 preferably is corrugated co-axial tubing which is well known in the art of anesthesia respiratory breathing circuits and which includes an inner corrugated sleeve or tube surrounded by an outer corrugated flexible sleeve or tube, with the inner tube adapted to carry inspired fresh gas and the outer tube adapted to carry exhaled gas to and from a patient through face mask 10. Thus, as best seen in FIG. 4, co-axial tube 136 includes an outer sleeve 142 and an inner sleeve 144 of reduced diameter relative to outer sleeve 142 suitably supported therein to define the first passage 146 (inhalation) surrounded by the second annular passage 148 (exhalation) as described in my prior application Ser. No. 12/658,019, filed Feb. 25, 2010 (herein sometimes "immediately prior application").

As further disclosed in my immediately prior application, the opposite or second end of the first length of coaxial-flexible tubing 136 is adapted to be suitably sealingly connected to T-connector 140 which also is of co-axial design and has an output branch 170 adapted to be connected to a one-way valve member or housing 172 and thence to the input collar of flexible exhalation reservoir bag 176, which bag, in turn, has an opening at its other opposed end. T-connector 140 also has an output branch 168 defining a receptacle adapted to be sealing and slidingly connected to the first output nozzle 126 of "Bag Tee" 124 of Flowmeter 100 preferably via a pair of suitable co-axial interfitting extension cylindrical tube adapters 186, 188.

The details of the T-connector 140, one-way valve member 172, and flexible exhalation reservoir bag 176 are more completely set forth in my immediately prior application, and that more complete explanation is hereby incorporated herein by this reference. Suffice it to say, as disclosed in my immediately prior application, the first length of co-axial flexible tubing 136 is connected at a first end to a respiratory face mask 10 which latter is adapted to be resiliently sealed on a patient's face, and at its other opposed end co-axial flexible tubing 136 is sealingly connected to a branched coupling. The branched coupling (e.g. T-connector 140), in turn, includes one branch for connection to the fresh gas supply nozzle of the "dental" set-up (inhalation) and a second branch for connection to a flexible flow-through reservoir bag 176 (exhalation). A one-way valve (member 172) is disposed between the second branch output nozzle and the input of the flexible bag. The output of the flexible flow-through bag is suitably connected to the vacuum module of the "dental" set-up. The second branch of the coupling, the one-way valve, and the flexible flow-through reservoir bag define the exhalation limb of the breathing circuit. Fresh gas is drawn through the first branch coupling, the flexible co-axial tubing and flows into the mask to be inhaled by a patient whereas any exhaled or waste gas flows back through the flexible co-axial tubing, the second branch coupling, the one-way valve, the flexible flow-through reservoir bag and ultimately to the vacuum module of the "dental" set up. Hence, these parts work, the same way in connection with the uniquely modified circuit 90' as they do in connection with breathing circuit 90 of my immediately prior application.

Generally speaking, the vacuum suction flow rate made available by wall outlets in hospital venting systems and by the Flowmeter exemplified by the Porter MXR is relatively large, say on the order of up to about 40-50 liters/minute. This compares to a typical flow rate of gas through an anesthesia face mask when properly sealed on a patient's face of less than half or up to about 10-15 liters/min. In order to provide restrictionless breathing through the face mask 10 and its associated breathing circuit when connected to the vacuum nozzle of the Flowmeter (i.e. avoid competing with the patient's breathing for gas flowing through the circuit and mask), a vacuum relief member 62 is provided as disclosed in the prior alternatively preferred embodiments of my prior applications. Thus, as fully disclosed in my prior applications, this member 62 includes a suitable external opening to the room environment and is effective to draw (suction) fresh air into the exhalation limb prior to the connection to the vacuum nozzle 118 on the AVS of the Flowmeter. By this arrangement, the effective suction (flow rate) is reduced sufficiently to avoid collapse of the exhalation bag and/or competition for fresh gas elsewhere in the breathing circuit and especially when the patient inhales fresh gas through the mask and circuit. In essence, in my prior preferred embodiments, a portion of the vacuum suction is wasted by suctioning room air through an opening provided in the exhalation limb of the breathing circuit (e.g. member 162, collar 80, arrow 194).

In accordance with the new and improved alternatively preferred embodiments of the present application, the vacuum compensator 62 and collar 80 are dispensed with in their entirety, and the full vacuum or suction made available through the Flowmeter and AVS nozzle 118 is utilized by the suitable unique means disclosed herein for the dual purpose of (i) scavenging patient-exhaled air or gas in and through flexible reservoir bag 176 as before, and (ii) additionally vacuuming or suctioning ambient or room air proximal to the connection of the breathing circuit 90' at the inlet port 26 of the face mask 10. Hence, any gas escaping around the periphery of the mask by inadvertent displacement of the mask while it is fitted on the patient's face (accidentally or otherwise), in accordance with the present invention immediately, continuously and automatically will be suctioned or "vacuumed up" by the novel vacuum attachments associated with breathing circuit 90' as disclosed in the present application.

In one broad aspect therefore, the apparatus responsible for achieving the foregoing advantageous result according to the present invention comprises an ambient or room air suction member on or proximal to the mask inlet port 26 and/or the breathing-circuit-to-mask connection at a first end of breathing circuit 90'. In another broad aspect, the present invention comprises a supplemental flow passage, where one end of the supplemental flow passage is connected to a vacuum attachment or ambient air suction member, and the other end of the supplemental flow passage is connected directly or indirectly to a source of vacuum.

Figure 5:
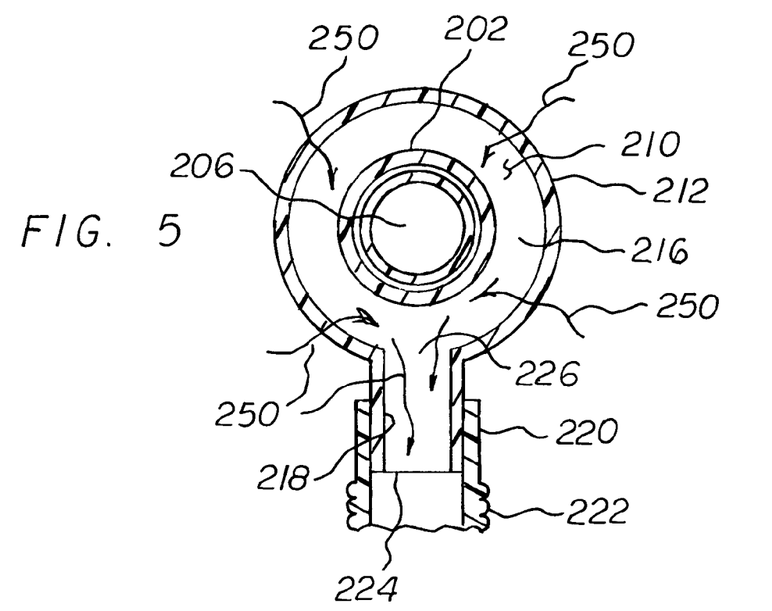
FIG. 5 is a cross-sectional view taken along line 5-5 of FIG. 4.

More specifically, as substantially best depicted in FIGS. 3-5, the preferred vacuum attachment or ambient air suction member or nozzle, generally represented by reference numeral 208, comprises an annular flange portion 210 extending radially outwardly on first input end 202 of elbow connector 200 and further comprises an integral, annular wall or skirt portion 212 extending from flange portion 210 axially along first input end 202 terminating at its distal extremity in an annular edge 214 spaced a pre-determined distance "e" axially measured from the junction of the base of inlet port 26 on mask shell 20 when the first input end 202 of connector 200 is operatively coupled to face mask inlet port 26.

Preferably vacuum attachment 208 and connector 200 are fabricated as a unitary or "single-piece" breathing circuit elbow connector, as by plastic molding same using well known techniques. As depicted, in such a single part preferably the wall portion 214 of vacuum attachment 208 forms a concentric substantially cylindrically-shaped outer sleeve on the elbow connector with the sleeve being closed at one end on first input end 202 by virtue of flange 210 and which first input end 202 also is substantially cylindrically-shaped. The terms "radial," "radially," "axial," "axially," "concentric," "cylindrical" or "cylindrically" as used herein unless otherwise specified each is taken with reference to the imaginary common central axis of the through openings defined by mask inlet port 26 and/or first input end 202, respectively, when these parts are coupled together, as viewed in FIG. 4 for example.

By the foregoing construction, when the first input end 202 of elbow connector 200 is operatively coupled to face mask inlet port 26 by being inserted therein, the outer concentric sleeve, or more specifically, the annular flange portion 210 and annular wall portion 212 along with distal edge 214 define an annular-shaped suction chamber, duct or manifold 216 adapted to receive therein the substantially cylindrical wall of protruding face mask inlet port 26 and in so doing to surround or encircle the distal outer side portion of the mask inlet port 26 substantially as shown in FIGS. 3 and 4.

In turn, the annular mouth or opening of the resulting suction chamber defined by edge 214 encircles the mask inlet 26 and is adapted to be spaced the distance "e" from the mask shell 20 (see FIG. 4). It thus will be observed that the "suction annulus" formed or defined by the interior of suction chamber 216 encompasses the top or distal portion of the protruding inlet port 26 substantially as depicted in FIGS. 3 and 4, and extends axially toward the confronting surface of shell 20 terminating the aforementioned distance "e" from the mask shell 20. The suction annulus has a transverse or radial thickness measured by the distance the wall or skirt portion 212 extends radially with respect to the outside surface of inlet port 26. In the position of the parts depicted in FIGS. 3 and 4, suction chamber 216 is closed at one axial end by flange portion 210 and has an annular-shaped "radially extending" opening or mouth at its at other opposed axial end defined by edge 214, which opening confronts the crown of face mask shell 20 in what may be characterized as an annular-shaped or substantially 360 degree pattern substantially encircling the base of protruding face mask inlet port 26.

Extending radially from wall or skirt portion 212 on one outer circumferential side thereof and proximal to radial flange 210 as substantially shown in FIGS. 3 and 4 is a preferably cylindrically-shaped tubular extension 218 which defines a connection nipple for cuff 220 of one end of a length of supplemental, preferably corrugated, flexible tubing 222 (non-co-axial). Tubular extension 218 has a mouth or opening 224 at its distal end and communicates at its opposite end with the annular-shaped suction chamber 216 through a suitable, preferably cylindrically-shaped opening 226 in wall portion 212. By the foregoing construction, tubular extension 218 defines a passageway or continuous flow path extending from the vacuum attachment 208 and more specifically, from the annular opening defined by annular skirt edge 214, through the suction chamber or annulus 216, through opening 226 into tubular extension 218, and finally though opening or mouth 224 of extension 218 into the one end of supplemental flexible tubing 222.

In accordance with the present invention, and as schematically best depicted in FIG. 1, supplemental flexible tubing 222 is provided of sufficient length to extend generally along the longitudinal extent of flexible co-axial tubing 136 until the cuff 223 on the opposed other end of supplemental tubing 222 ultimately is sealingly connected to one arm 230 of a breathing circuit Y-connector generally represented by reference sign 232. Supplemental flexible tubing 222 preferably is of the well-known single-lumen corrugated type, but may alternatively be of the smooth type as well.

Breathing circuit Y-connectors are well known in the art and typically comprise a plastic molded part (e.g. PVC or polypropylene) having internally intersecting through-passages defined by the three arms thereof. Thus, air or gas flowing through one arm of the Y-connector will flow through the other two arms as well. Y-connector 232 has a second arm 236 sealingly connected to a length of flexible "exhalation" tubing 238 to be explained in more detail below, and has a third arm 240 sealingly connected to one end of flexible tubing 76 which as before is adapted to be sealingly connected at its other end to the mask-to-vacuum nipple 118 of Flowmeter AVS 114.

To facilitate ease in handling flexible tubes 136 and 222 and to produce a compact and neat unitary arrangement when elbow 200 is connected to face mask 10, supplemental tubing 222 may be tied or otherwise attached to flexible tubing 136 along a substantial portion of their common longitudinal extent via the use of suitable resilient plastic attachment clips 234 spaced at convenient intervals, as substantially schematically depicted in FIG. 1. If desired, in lieu of such clips 234, tubes 136 and 222 alternatively may be taped together at spaced intervals using suitable bands of adhesive tape or the like.

Figure 6:
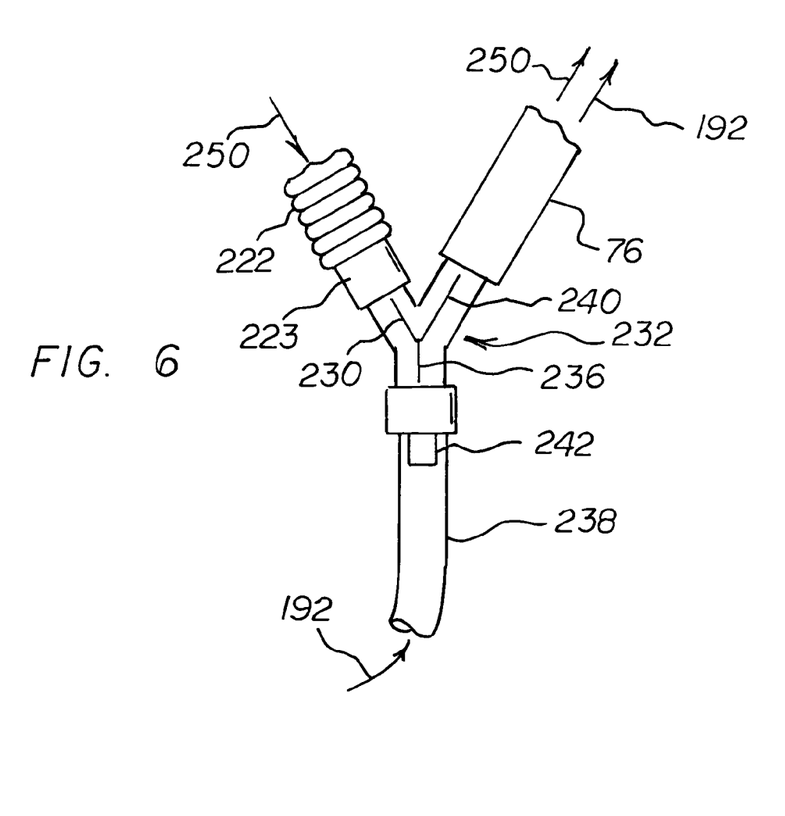
FIG. 6 is an enlarged view in elevation of the Y-connector 232 shown in FIGS. 1 and 2.

With continued reference to FIGS. 1, 2 and 6, it will be observed that the opposite end of exhalation tubing 238 is suitably sealingly and securely connected to flexible reservoir bag 176 through an opening in the bottom of the bag (not labeled). Hence, flexible tubing 238 provides a continuous flow path or passageway for any exhaled or waste gas exiting flexible bag 176 which passageway extends from bag 176 to the arm 236 of Y-connector 232.

In accordance with the invention, the length of flexible exhalation tubing 238 has a smaller diameter through-bore than that of supplemental tubing 222. Likewise arm 236 on Y-connector 232 has a correspondingly smaller diameter nipple 242 to which tubing 238 is to be sealingly connected. Owing to this arrangement, the suction present in flexible tubing 76 when it is connected to nozzle 118 of the AVS 114 is reflected unevenly in arms 230, 236 of Y-connector 232 with a proportionally greater suction being applied to the arm with the larger diameter, i.e. arm 230 will have a relatively greater suction applied to it manifested in a greater flow rate therethrough because the smaller diameter arm 236 (and the length of tubing 238) offers increased resistance to flow. In carrying out the present invention, it is preferred that approximately 60% of the total suction available in tubing 76 be reflected in arm 230 of Y-connector whereas about 40% will be reflected in arm 236. This relative disparity conveniently may be varied one way or another if so desired by increasing the resistance to flow afforded by tubing 238, say by increasing or decreasing its length. That is, if it is desired to decrease the proportion of the total suction applied to or in tubing 238, then the restriction to flow in the passageway extending between bag 176 and Y-connector 232 can be increased. Conversely, if it is desired to increase the proportion of the total suction applied to or in tubing 238, then the restriction to flow in the passageway extending between bag 176 and arm 236 of Y-connector 232 can be decreased. Such increase or decrease may be effected by varying the length and internal diameter of tubing 238 and correspondingly the diameter of the input arm 236 of Y-connector 232.

For purposes of illustrating the present invention, and without limitation, it is preferred that tubes 222 and 76 have an internal diameter of about 10 mm, and that tube 238 has an internal diameter of about 6.5 mm and a longitudinal extent or length of about 37 cm. With respect to Y-connector 232, arms 230 and 240 have an internal diameter of about 10 mm and arm 236 (nipple 242) has an internal diameter of about 6.5 mm. When such dimensions are employed, the Y-connector 232 divides or diverts approximately 60% of the total suction available at nozzle 118 of AVS 114 to arm 230 and tubing 222.

From the foregoing, it will be apparent that when tubing 76 is sealing connected to nozzle 118, Y-connector 232 functions as a "gas flow junction" dividing the total suction made available at nozzle 118 between the "exhalation limb" of the breathing circuit 90' on the one hand, and the ambient air suction member 208 on the other hand. Flexible tubing 238, like flexible tubing 76, preferably can comprise either corrugated flexible tubing or smooth (PVC) tubing, with smooth flexible tubing being mostly preferred.

With respect to the manner of operation of the present invention, as before, the first end of the flexible co-axial tubing 136 first is sealingly connected to face mask 10 by inserting the first input end 202 of elbow connector 200 into the inlet port 26 of the face mask making such that the clearance space "e" is present between the bottom edge of 214 of suction nozzle 208 and the juncture of the inlet port 26 and the face mask shell 20 (see FIG. 4). Next, the T-connector 140 is sealing and slidingly connected to the first output nozzle 126 of "Bag Tee" 124 of Flowmeter 100 preferably via the pair of the co-axial interfitting extension cylindrical tube adapters 186, 188. Then, the distal end of breathing circuit 90', namely flexible tube 76 is slidingly and sealing inserted onto mask-to-vacuum nozzle 118 of AVS module 114. When these three steps are complete, the breathing circuit 90' and face mask 10 assembly is sealing coupled to Flowmeter 100 and appears substantially as depicted in FIG. 1.

After assuring the presence of a vacuum on line 122, mask 10 next may be fitted to a patient's face. Before doing so however, it is desirable to cause oxygen to flow through the mask and this can be accomplished by suitable manipulation of control valve 104 on Flowmeter console 102 or by pressing the oxygen "flush" button 190 on the Flowmeter console 102 which causes oxygen to flow through the Bag Tee 124 filling reservoir bag 132 with oxygen. Following application of the mask 10 to a patient's face and after assuring that the mask is in sealing engagement therewith, control valve 106 may then suitably be manipulated to cause nitrous oxide to flow through the Flowmeter and produce a desired, selected concentration or mixture ratio of nitrous to oxygen, typically up to about 70%, into the flexible reservoir bag 132 through nozzle 116 and ultimately through output nozzle 128 as schematically, indicated by arrow 134 (FIG. 2). The foregoing flow of fresh gas (or mixture of gas) through output nozzle 128 is effected immediately upon inspiration by the patient through sealed-on-the-face mask 10, because this action opens the demand valve in output nozzle 128 releasing the gas or gas mixture stored in flexible reservoir bag 132. The path of fresh inhaled gas ("inhalation path") is indicated more graphically in FIGS. 1, 2 and 4 where arrows 134 represent the flow of the fresh gas entering T-connector 140 from the reservoir bag 132, then inner sleeve 144 of co-axial tubing 136, and finally through passageway 206 of elbow 200 and port 26 into the interior of face mask 10.

Upon exhalation by the patient, the exhaled waste gas travels a different path. This path is schematically indicated by arrows 192 which represent exhaled waste gas flowing through port 26 of face mask 10, passageway 206 of elbow connector 200, outer sleeve 142 of co-axial tubing 136, then through T-connector 140, the output port 170 of the T-connector 140, one-way valve member 172 and into flow-through flexible reservoir bag 176. As pointed out in my immediately prior application, in accordance with the present invention, the flexible flow-through reservoir bag 176 is employed exclusively to store exhaled waste gas. Bag 176 receives such flow of gas only when the patient exhales through mask 10 and one-way valve 174 is in an "open" condition. When the patient inhales through mask 10, valve 174 remains closed and substantially no exhaled gas stored in flexible reservoir bag 176 can be re-breathed by the patient. Rather, any waste gas stored in bag 176, by the action of the vacuum on line 122 is evacuated from bag 176 along the path comprising the opening in the bottom of bag 176, flexible tubing 238, arms 236 and 240 of Y-connector 232, flexible tube 76, mask-to-vacuum nipple 118, and vacuum-to-source output nozzle 120 (see FIGS. 1, 2, 4 and 6).

In accordance with the invention, during both the inhalation and exhalation phases, i.e. at all times when there is a vacuum on line 122, the suction nozzle 208 is effective to create an annular zone of negative pressure proximal to the breathing circuit connection to the mask inlet port 26. This zone of negative pressure, in turn, is effective to "vacuum up" or suction the ambient or room air externally surrounding the mask in a flow pattern that is directed over the shell of the mask toward the mask inlet port 26. This suctioned flow of ambient room air, indicated by arrows 250 (FIGS. 3-6), creates a current of "scavenged" ambient air continuously being drawn into the mouth of the annular chamber 216 defined by wall or skirt portion 212 of suction member 208. The scavenged ambient air stream 250 travels through opening 226, the passageway defined by extension 218, through flexible tubing 222, and arm 230 of Y-connector 232. The scavenged ambient air 250 next enters arm 240 of the Y-connector, mixes with the exhaled waste gas 192 flowing therein and finally is evacuated along with the waste gas through mask-to-vacuum nozzle 118 and vacuum-to-source output nozzle 120.

From the foregoing description, the present invention retains all of the advantages of my prior embodiments, but includes the further advantage of including new and improved means for automatically immediately scavenging, vacuuming, suctioning and evacuating through a self-contained closed circuit any gases escaping from the periphery of the mask 10 in the event the mask is displaced from sealing engagement with the patient's face by accident or otherwise and before such gases can contaminate the environment. The apparatus disclosed herein therefore is advantageously suited for use in any hospital or clinical setting where there exists the requirement of avoiding the build-up of any such gas or gases in the room environment.

Figure 7:
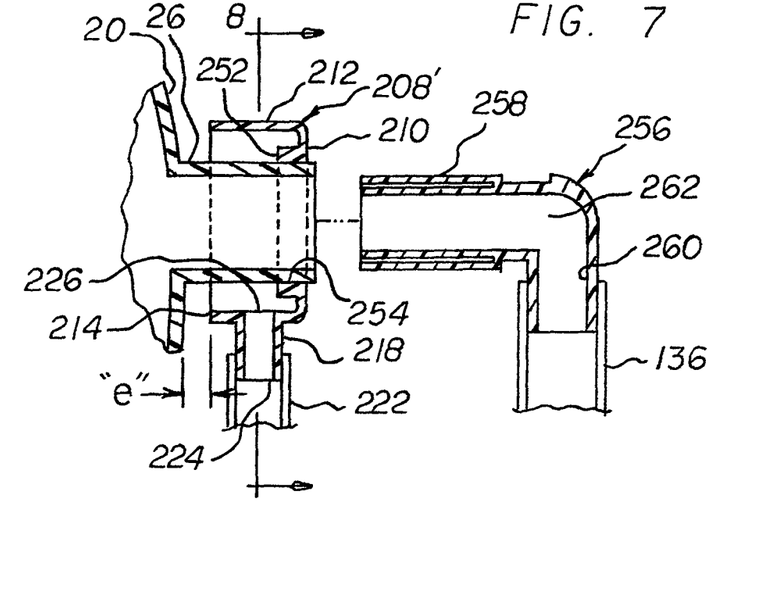
FIG. 7 is a cross-sectional view in elevation of a second alternatively preferred embodiment of the present invention showing the suction member or nozzle 208' as a separate part mounted directly on the face mask inlet port extension 26, and further showing in exploded cross-sectional view a conventional breathing circuit elbow connector 256 with which the alternatively preferred embodiment may be used.
Figure 8:
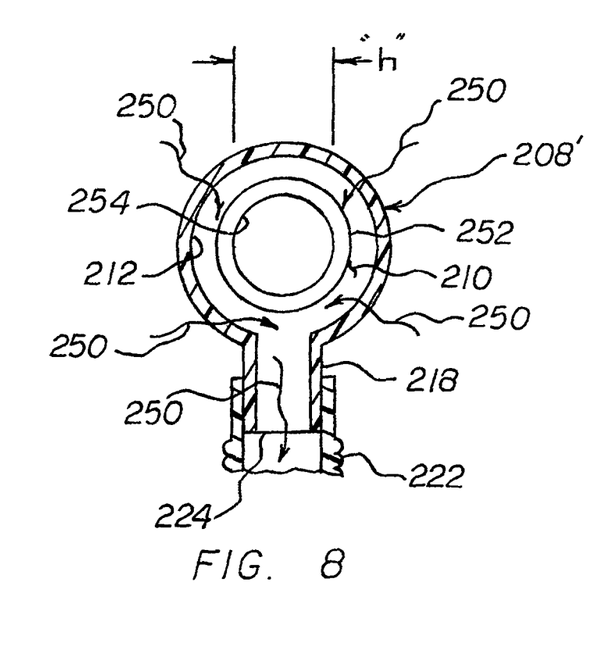
FIG. 8 is a cross-sectional view taken along line 8-8 of FIG. 7.

As disclosed above, the alternative embodiment of FIGS. 1-6 preferably features a breathing-circuit-to-face-mask connector where the vacuum attachment or suction nozzle 208 is integrated with the breathing circuit connector 200. Turning now to FIGS. 7 and 8, wherein like reference numerals represent similar parts already disclosed, in lieu of fabricating the breathing-circuit-to-mask connector and the suction nozzle as an integrated unitary molded plastic part as (preferred in regard to FIGS. 1-6), the annular suction nozzle 208' alternatively can be formed as a separate part, preferably as a plastic molded separate part which, in turn, can be mounted separately directly on or in relation to the outer surface of the protruding face mask inlet port extension 26 substantially as depicted in FIG. 7. To facilitate such separate direct mounting capability, separate nozzle part 208' comprises a central annular substantially cylindrically-shaped hub portion 252 from which the flange 210 radially extends, and as before, an annular wall or skirt portion 212 affixed to the radial outer extremity of the flange 210 is provided extending substantially parallel and axially to the imaginary central axis defined by hub portion 252, ultimately terminating at its axial extremity in the peripheral annular edge 214. The central opening defined by axial hub wall portion 254 has a diameter "h" which is sized and configured such that when the separate nozzle 208' is place over and upon the protruding face mask inlet extension 26, there is a tight frictional fit between hub and the outer surface of the inlet extension sufficient to maintain annular nozzle 208' in the position substantially as depicted in FIG. 7. Alternatively, nozzle 208' may be provided with an axial tubular hub extension (not shown) of sufficient length to support the nozzle the distance "e" from shell 20, or even be provided with a loose "hub fit" relative to extension 26 because of the concave shape of the mask shell.

In operation, the separate annular nozzle part 208' comprising hub portion 252, radial flange 210, wall portion 212, and tubular extension 218, is first placed on the exterior of the face mask inlet 26 substantially as shown in FIG. 7. Then a conventional breathing circuit elbow connector 256 on breathing circuit 90' having a first end 258, an opposed second end 260, and an interior through-passage 262 is sealingly inserted into the mask inlet port 26 as substantially and diagrammatically indicated in FIG. 7. The alternatively preferred annular nozzle 208' thus functions, in the same manner as the above-described alternatively preferred embodiment of FIGS. 1-6, namely to create a zone of negative pressure proximal to the breathing circuit connection to the mask inlet port 26 effective to "vacuum up" or suction the ambient or room air externally surrounding the face mask in a flow pattern indicated by arrows 250 (FIG. 8). And as before, The scavenged ambient air stream 250 travels through opening 226, the passageway defined by extension 218, through flexible tubing 222, to the source of vacuum present at arm 230 of Y-connector 232.

As used herein and in the annexed claims, the phrases "scavenging," "suctioning," "evacuating" "vacuuming" or "vacuum suction" are to be employed synonymously to refer to the action of ambient (room) air 250 being drawn into vacuum attachment or suction members 208 or 208' under the influence of a vacuum derived for a vacuum source.

While preferred embodiments of the present invention have been disclosed in connection with the Porter MXR Flowmeter "dental" set-up, it will be appreciated that the present invention may be employed with other dental set-ups or gas devices having a nitrous oxide "sedation" capability as well. Thus, for example, the vacuum attachments and breathing circuit apparatus disclosed in this application also may be used with the "Digital Flowmeter" commercially distributed by Accutron Inc., Phoenix, Ariz.

Similarly, while the use of co-axial flexible 136 tubing between the elbow connector 200 and T-connector 140 provides a more compact and streamlined breathing circuit and helps to avoid snagging and crimping of the fresh gas supply, it will be appreciated that separate single-lumen flexible tubes, either of the corrugated or smooth type may be used for the fresh gas supply and the exhaled waste gas, respectively, without departing from the principles of the invention.

From the foregoing description, it should be evident that the disclosed alternatively preferred embodiments of the present invention solve the vexing problem of providing a suitable "full" face mask and breathing circuit for administering anesthesia gases or other gases employing the relatively portable and inexpensive gas supply and scavenging equipment heretofore used only in the practice of dentistry. By using such a "full" face mask in conjunction with the breathing circuit and vacuum attachments of the present invention build-up of waste gas in the clinical room is minimized. As a result, "sedation" anesthesia employing nitrous oxide is facilitated in hospitals, surgical centers and doctor's offices in a safe and effective manner thereby leading to increased patient satisfaction and reduced medical costs.

Many variations and modifications to the foregoing will be readily apparent and obvious to one skilled in the art, and all equivalent relationships to those illustrated in the drawings and described in the specification are intended to be encompassed by the present invention. Therefore, it is not desired to limit the invention to the exact construction and operation shown and described, and accordingly, all suitable modifications and equivalents may be resorted to, falling within the scope of the invention as defined in the annexed claims.

The face mask and breathing circuit embodiments of the present invention are intended to be disposable and are intended for a single use to avoid cross-contamination. The components of the respiratory face mask and breathing circuit assemblies of the present invention can be made from inexpensive and durable plastic or metal materials. The face mask, breathing circuit or ambient air suction member or nozzle components of the present invention may be packaged together as a kit or provided in separate packages, respectively.

The connector components shown in the drawings are diagrammatically depicted for the sake of illustration and not drawn to scale. It will be appreciated that the precise dimensions for breathing attachments used in anesthetic and respiratory equipment recommended in ISO Standard ISO 5356-1:2004, incorporated herein by this reference, advantageously can be used in carrying out the present invention.

As to the manner of usage and operation of the instant invention, the same is apparent from the above disclosure, and accordingly, no further discussion relative to the manner of usage and operation need be provided.

What is claimed as being new and desired to be protected by Letters Patent of the United States is as follows:

1. A breathing circuit apparatus for use with an anesthesia mask, a gas supply and a vacuum source, comprising:

said anesthesia mask including a mask body and a port projecting therefrom;

a mask-to-vacuum attachment member mounted in engaging relation to said port;

said mask-to-vacuum attachment member having a first port and a second port;

a first tube having a first end engaging said first port of said mask-to-vacuum attachment member so that said first tube is adapted to provide fluid communication between said anesthesia mask and said gas supply;

a flexible exhalation bag having an inlet and an outlet;

a second tube having a first end engaging said first port of said mask-to-vacuum member, said second tube being coaxial with said first tube along a predetermined extent of said first tube and said second tube adapted to provide fluid communication between said anesthesia mask and said inlet of said exhalation bag;

a one-way valve positioned between said anesthesia mask and said inlet of said exhalation bag to prevent re-breathing of exhaled gases;

a gas flow-junction member having a first inlet, a second inlet, and an outlet;

a third tube connected between said outlet of said exhalation bag and said first inlet of said gas flow-junction member, said third tube reducing the magnitude of the vacuum sufficiently to avoid collapse of said flexible exhalation bag by said vacuum source;

a fourth tube adapted to be connected between said outlet of said gas flow-junction member and said vacuum source;

a fifth flexible tube disposed in fluid communication between said second port of said mask-to-vacuum attachment member and said second inlet of said gas flow-junction member;

said port of said anesthesia mask defining a common flow passage for fresh gas and exhaled gas;

said mask-to-vacuum attachment member having a cylindrical structure;

at least one inlet opening formed in said cylindrical mask-to-vacuum attachment member;

said at least one inlet opening being in open fluid communication with ambient air so that said ambient air is drawn through said fifth tube and through said second inlet of said gas flow-junction member and into said vacuum source;

said fifth tube having a restriction to flow that is greater than a restriction to flow of said third tube so that the vacuum suction in said third tube is greater than the vacuum suction in said fifth tube; and the vacuum suction in said third tube being about 60% of the suction produced by said vacuum source when said outlet of said gas flow-function member is operatively coupled to said vacuum source by said fourth tube;

whereby gas that may leak from said anesthesia mask is drawn into said vacuum source so that said gas that may leak from said anesthesia mask cannot be re-breathed by the patient or other persons in the vicinity of said patient.

* * * * *